United States Patent [19]

Levy et al.

[11] Patent Number: 4,780,321

[45] Date of Patent: Oct. 25, 1988

[54] MICROCAPSULES HAVING MIXED WALLS FORMED OF RETICULATED POLYHOLOSIDES AND PROTEINS AND PROCESS FOR PREPARATION THEREOF

[75] Inventors: Marie Christine Levy, Reims; Bertrand Gourdier, Rilly la Montagne, both of France

[73] Assignee: Centre National de la Recherche Scientifique (CNRS), Paris, France

[21] Appl. No.: 894,383

[22] Filed: Aug. 7, 1986

Related U.S. Application Data

[63] Continuation of Ser. No. 496,114, May 19, 1983, abandoned.

[30] Foreign Application Priority Data

May 26, 1982 [FR] France .............................. 82 09156

[51] Int. Cl.⁴ .............................................. B32B 5/16
[52] U.S. Cl. .................................. 424/499; 264/4.32; 428/402.2
[58] Field of Search ....................... 424/35, 36, 37, 19, 424/499; 264/4.32; 428/402.2

[56] References Cited

U.S. PATENT DOCUMENTS 3,578,605  5/1971  Baxter .................................... 424/37
4,138,362  2/1979  Vassiliades et al. ................... 424/36

FOREIGN PATENT DOCUMENTS 1415039  10/1964  France .
2275250   5/1975  France .
2040863   9/1980  United Kingdom .

OTHER PUBLICATIONS

M. C. Levy et al.–2nd Congress Int. Technol. Pharm. Paris–1980, III, pp. 15–24.

Primary Examiner—Joseph L. Schofer
Assistant Examiner—Peter F. Kulkosky
Attorney, Agent, or Firm—Ladas & Parry

[57] ABSTRACT

A process for preparing microcapsules containing a pharmaceutically active substance of a water soluble nature is provided, which involves dissolving a mixture containing at least one water soluble polyholoside or water soluble derivative of a polyholoside, at least one protein, and the pharmaceutically active substance in an alkaline aqueous solution having a pH preferably above 10, the solution being emulsified by dispersion within an immiscible organic solvent, by addition of an emulsifier of the water in oil type and by stirring. Thereafter, a reticulation agent dissolved in the same immiscible organic solvent is added to the previously obtained emulsion being stirred, and the stirring is continued until interfacial reticulation is achieved. The microcapsules are then isolated by diluting the reaction mixture with solvent, or a mixture of solvents and then centrifugation or decantation.

15 Claims, 1 Drawing Sheet

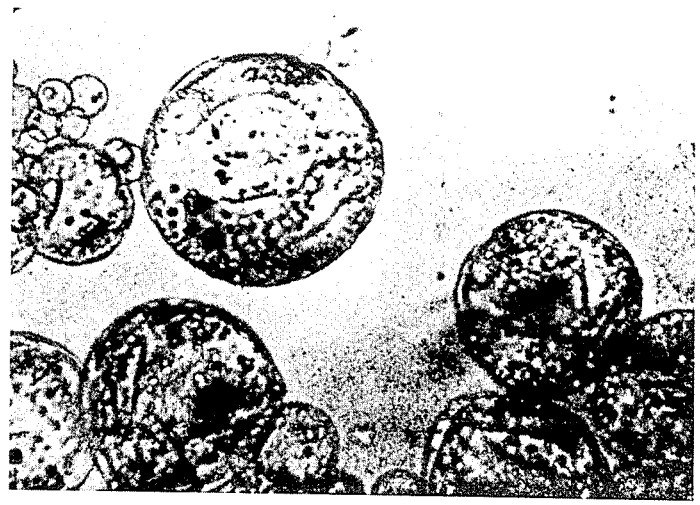
FIG_1
FIG_2

MICROCAPSULES HAVING MIXED WALLS FORMED OF RETICULATED POLYHOLOSIDES AND PROTEINS AND PROCESS FOR PREPARATION THEREOF

This is a continuation of co-pending application Ser. No. 496,114 filed on May 19, 1983 and now abandoned.

This invention concerns itself with microcapsules having a mixed wall obtained by reticulating a mixture containing on one side at least one water-soluble polyholoside or water-soluble derivative of polyholoside and on the other at least one protein, and process of preparation thereof.

The microcapsules according to the invention are characterized by the fact that the mixed external wall of the microcapsules is obtained by interfacial reticulation of a mixture comprising at least one water-soluble polyholoside or water-soluble derivative of polyholoside and at least one protein by means of a reticulating agent constituted by an acylating bifunctional reagent.

BACKGROUND OF THE INVENTION

This invention concerns itself with microcapsules having mixed walls obtained by reticulating a mixture of at least one water-soluble polyholoside or water-soluble derivative of polyholoside and at least one protein, and the process of preparation thereof. The invention refers to microcapsules including in particular, but not exclusively, a pharmaceutically active substance. The microcapsules according to the invention may in effect include also other substances such as food substances and in particular essential oils.

It will be briefly recalled in the first place that microcapsules are artificial organites that are of very great interest for galenically forming different medicaments. The inclusion of an active principle in a microscopical spherule makes it possible in fact to ensure its transitory protection in respect to denaturing agents such as digestive enzymes.

In other cases the wall of the microcapsules modulates the diffusion of the active principle, which is taken advantage of in the manufacture of galenic molds of prolonged or delayed action. It is necessary for the wall of the spherule to have all the guarantees of innocuousness related to the use in human therapy.

SUMMARY OF THE INVENTION

The object of this invention perfectly meets the conditions above stated. The microcapsules according to this invention are characterized by including a mixed external wall obtained by interfacial reticulation between at least one water-soluble derivative of polyholoside or a water-soluble polyholoside, at least one protein, and a reticulating agent particularly constituted by an acylating bifunctional reagent.

BRIEF DESCRIPTION OF THE DRAWINGS

FIG. 1—Optical micrograph of the microcapsule of the invention.

FIG. 2—Electron micrograph of the microcapsule of the invention.

DESCRIPTION OF THE PREFERRED EMBODIMENTS

According to this invention those microcapsules can be obtained from water-soluble polyholosides or from water-soluble derivatives of polyholosides and from at least one protein by putting into play the following three successive stages:

(i) at least one water-soluble polyholoside or water-soluble derivative of polyholoside, at least one protein, and the pharmaceutically active substance are dissolved in an alkaline aqueous solution having a pH preferably above 10, which is emulsified by dispersion within an immiscible organic solvent by addition of an emulsifier and by stirring;

(ii) to the emulsion thus obtained, which is always stirred, there is added a reticulating agent dissolved in said immiscible organic solvent and the stirring is continued until obtaining an interfacial reticulation, and (iii) the microcapsules are isolated by diluting the reaction mixture by means of a solvent or of an appropriate mixture of solvents followed by a succession of decanting and/or centrifuging steps and washing steps.

The water-soluble polyholosides or water-soluble derivatives of polyholosides used within the framework of this invention likewise include the natural water-soluble polyholosides such as gum arabic or gum guar, and polyholosides modified in order to make them water-soluble, for example, by treatment with acid or alkaline solutions or also by chemical grafting of hydrophilic lateral chains. Those treatments for modifying the polyholosides in order to make them water soluble or to transform them in water-soluble derivatives of polyholosides are well known to those skilled in the art. Merely by way of example let mention be made of the alkali-cellulose obtained by treatment of the cellulose with the aid of a soda lye, the soluble starch obtained by degradation of the starch, the same as the dextrans of low molecular weight obtained by degradation of the dextrans. Let likewise be cited the hydroxypropyl cellulose as an example of water-soluble derivatives of polyholosides resulting from the chemical grafting of hydrophilic lateral chains.

Within the scope of this invention, said water-soluble polyholosides or water-soluble derivatives of polyholosides can be used alone or intermixed in association with at least one protein such as casein and gelatin.

This invention is mainly applied to the microencapsulation of pharmaceutically active substances of water-soluble nature and in particular to the alkaline salts of carboxylic acids such as salicylic acid and derivatives thereof.

Other characteristics and advantages of this invention will become apparent from the reading of the detailed description made herebelow, specially with reference to some particular examples of putting into practice the process of the invention, which examples are given as simple illustration.

According to this invention, the microcapsules are obtained from water-soluble polyholosides or water-soluble derivatives of polyholosides mixed with at least one protein and to which is applied the microencapsulation process by emulsion-reticulation developed by M. C. Ley and colleagues (RAMBOURG (P)): "On the microencapsulation of invertase and hemoglobin: interfacial polymerization by the process of emulsion-reticulation". Doctoral Thesis, 3rd cycle, Paris-South University, U.E.R. Therapeutical Chemistry, 1980, Levy (M. C.), RAMBOURG (P) and Levy (J), 2nd Int. Congress of Technol. Pharm., Paris 1980, III, 15–24 Microencapsulation II).

This microencapsulation process according to the invention is subdivided in three successive stages, namely:
(i) a first stage of emulsification of the mixture of water-soluble polyholosides or water-soluble derivatives of polyholosides and at least one protein;
(ii) a second stage of interfacial reticulation, and
(iii) a third stage of isolation of the microcapsules.

During the first stage of emulsification, an alkaline aqueous solution of the substance to be encapsulated, of the water-soluble polyholoside or water-soluble derivative of polyholoside, and of the protein is dispersed in fine globules within an immiscible organic solvent.

The aqueous solution is alkalinized, for example, by adding sodium hydroxide until obtaining a concentration of about 0.5M so as to arrive at a pH preferably above 10.

The organic solvent used during this first emulsification stage is advantageously selected in a manner such that it be immiscible in water, that its density be substantially comprised between 0.7 and 1.1, and that the reticulation agent used in the second stage dissolves in it. There is advantageously used, for instance, a binary mixture constituted by a chlorinated hydrocarbon having one or two carbon atoms such as chloroform, methylene chloride, or trichloroethylene, and by a non-chlorinated hydrocarbon including from 5 to 7 carbon atoms such as hexane or cyclohexane.

The emulsifier used during this first stage is a surfactant such as a sorbitol or fatty acid ester or any other surfactant chosen by those skilled in the art in order to prepare an emulsion of the water-in-oil type. The sorbitol trioleate (Span 85 ®) is advantageously used. But it must be noted that due to the alkalinity of the solution to be emulsified, cationic surfactants must be conveniently avoided preferring non-ionic surfactants.

The relative concentrations, volume and quantities of the aqueous solution, of the organic solvent and of the emulsifier that make it possible to obtain the emulsion capable of being subsequently reticulated can be adapted with great latitude and remarkably depart from the proportions indicated in the examples described below.

Such an emulsion can be easily obtained, for instance, by means of a metallic helix of 5 blades (each 20 mm long) mechanically drawn to the interior of a 100 ml. beaker. A rotation speed between about 1000 and about 2000 revs. per minute maintained for at least three minutes approximately is then sufficient for carrying out the emulsification.

In the second stage of interfacial reticulation, the wall of the microcapsules is formed by reticulation in particular by means of an acylating bifunctional reagent such as carboxylic diacid halide, a diisocyanate, where the two functional groups are carried by an aromatic cycle or separated by an aliphatic chain of from 2 to 10 carbon atoms, or one is carried by an aromatic cycle and the other by a juxtanuclear aliphatic chain, for example, terephtaloyle dichloride, toluene diisocyanate, hexamethylene diisocyanate.

The reticulation agent is added, dissolved preferably in the organic solvent already used in the first stage, to the emulsion that has been kept under stirring.

This operation is effected at a temperature between the freezing point and the boiling point of the liquids used, most frequently at ordinary temperature.

A concentration of the reticulating agent in the solvent mixture that varies the saturation to a concentration 0.1M is compatible with the obtention of microcapsules. Conditions favorable to the preparation of microcapsules are generally obtained when the solution of the reticulating agent is added to the emulsion in a volume substantially equal to the volume of solvent that served to prepare said emulsion.

Stirring is continued until an examination with the optical microscope shows the formation of individualized microcapsules, which requires an average duration of from about 3 to about 30 minutes.

The third stage of isolation of the microcapsules is carried out by diluting the reaction mixture by means of a solvent or a mixture of solvents, then subjecting the suspension of microcapsules to a succession of decantations and washings.

The decantation can be replaced to advantage by a centrifugation, for example, $350 \times g$, 30 seconds.

The microcapsules are washed in a solvent selected for not carrying the microencapsulated substances such as ethyl ether, ethyl alcohol and acetone.

The dry microcapsules are obtained by evaporation of the ether, alcohol or acetone.

In the examples given below that illustrate the preparation of empty microcapsules, the washing has been effected, for example, by means of a solution of polysorbate (Tween 20 ®) in distilled water, then by means of pure water. Dry capsules can then be obtained after lyophilization.

The microcapsules of mixed walls according to the characteristics of the invention appear in optical microscopy in the form of well-individualized spherules the diameter of which can fluctuate between 25 and 300$\mu$. Spherules of larger size can be obtained when the emulsification and reticulation operations are carried out at a stirring speed of less than 1000 revs. per minute. A thick membrane of from about 1 to about 2$\mu$ is visible.

In sweeping electronic microscopy they have a continuous wall.

The microcapsules prepared according to the characteristics of the invention having a base of hydroxypropyl cellulose withstand without alteration a 10-hour incubation in artificial gastric medium (U.S.P. XIX), the same as a 10-hour incubation in artificial intestinal medium (U.S.P. XIX). Those capsules allow the product that has been encapsulated slowly to diffuse through their wall. These properties are applied to the preparation of medicaments in a galenic form of prolonged action.

According to the invention, variable proportions of a protein such as casein and gelatin are added to the water-soluble polyholosides or water-soluble derivatives of polyholosides in the course of the first emulsification phase. There are thus obtained microcapsules of mixed walls constituted at the same time of reticulated polyholosides and of reticulated protein. Such microcapsules prepared according to the characteristics of the invention, for example, from hydroxypropyl cellulose and from casein, remain unchanged after a 10-hour incubation in artificial gastric medium (U.S.P. XIX), but their walls undergo lysis after an incubation of approximately 6 hours in artificial intestinal medium (U.S.P. XIX). The properties of these microcapsules of mixed walls according to the invention are more particularly applied to the preparation of medicaments under a gastroresistant enterosoluble galenic form.

The examples that follow illustrate the object of this invention without limiting the applications.

EXAMPLE 1

Microcapsules of mixed walls prepared from hydroxypropyl cellulose (HPC) and from reticulated casein All the operations are carried out at ordinary temperature.

1. Emulsification

A solution of 3 g % (w/v) of HPC in soda 0.5N wherein have been dissolved 200 mg alkali-soluble casein is prepared by magnetic stirring at room temperature and continued for 2 hours.

There are placed in a 100 ml beaker 15 ml of a chloroform-cyclohexane mixture (1:4 v/v), hereinafter called solvent mixture, having added 0.30 ml sorbitol trioleate (Span 85 ®). The alkaline solution of HPC and casein is added, mechanically stirring (1000 revs. per minute) by means of a metal helix of 5 blades.

2. Reticulation

After 3 minutes, without interrupting the stirring, there are added 20 ml of a saturated solution of terephtaloyl chloride in the solvent mixture. Stirring is continued for 3 minutes.

3. Isolation of the microcapsules

The polymerization reaction is stopped by adding 30 ml of the solvent mixture in the reaction beaker. After manual stirring (glass stirrer) for a few minutes, the content of the beaker is distributed in two tubes of centrifugation.

After centrifuging for 30 seconds at 350×g, the supernatant is discarded. Each centrifugation residue is again put in suspension in 20 ml of a solution of 10% (v/v) of polysorbate (Tween 20 ®) in distilled water, then centrifuged (30 seconds, 350×g). After a new washing carried out under the same conditions, the centrifugation residues are washed with pure water.

4. Lyophilization

The centrifugation residues are put again in suspension in 50 ml distilled water, frozen and lyophilized.

About 100 mg dry microcapsules are obtained. The microcapsules obtained appear, after rehydration, in the form of regular spheres of a diameter between 30 and 80μ.

The attached FIG. 1 shows a plate of optical microscopy (enlarged 300 times) of the microcapsules obtained according to Example 1.

The attached FIG. 2 shows a plate of sweeping electronic microscopy (enlarged 450 times) of microcapsules prepared according to Example 1.

In optical microscopy the microcapsules appear in the form of well-individualized spheres of a diameter between 20 and 200 micra (see FIG. 1). On the sweeping electronic microscope a membrane is visible, they appear like unbroken spheres. The irregular surface has depressions (see FIG. 2).

1. Gastroressistance test

The test conducted like in Example 1 shows no alteration of the microcapsules after 10 hours.

2. Test of enteric solubility

The microcapsules put to incubate in the artificial intestinal liquid (U.S.P. XIX) are progressively destroyed: lysis starts after about 30 minutes and spreads out progressively for about 6 hours.

Lysis is not produced if the artificial intestinal medium does not contain pancreatin.

EXAMPLE 2

Microcapsules of mixed walls prepared from hydroxypropyl cellulose (HPC) and from reticulated casein containing patented blue V Preparation of lots of microcapsules 200 mg alkali-soluble casein and then 10 mg of patented blue V are dissolved in 3 ml of a 3% (w/v) solution of HPC in aqueous soda 0.5N.

Three lots of microcapsules are prepared (see Table I). The differences show in the emulsification conditions:

*lot 1 is prepared with a low stirring speed (1000 rpm) in the presence of 2% Span 85 ® (0.30 ml per 15 ml solvent mixture)

*lots 2 and 3 are prepared at 1800 rpm in the presence of 5% Span ® (0.75 ml per 15 ml solvent mixture)

in the reticulation time: 3 minutes (lots 1 and 3) or 15 minutes (lot 2).

Tests of contents release

Each lot of microcapsules is suspended in one liter of water and subjected to mechanical stirring (40 rpm) in a balloon kept at 37°. Samples are periodically taken. The suspension is filtered on a cellulose membrane (0.22μ) and the clean liquid is subjected to a colorimetric analysis.

Results (stated in Table I herebelow)

*With this type of microcapsules of mixed walls of HPC and casein, the patented blue is slowly released since after 4 hours the amount of released colorant represents a maximum of 10% of the amount of encapsulated colorant (10 mg).

In addition, after 8 hours a maximum of 13% of patented blue is released (lot 3) and even after 24 hours only 22% at most of release is obtained (compared to 48% in the case of the microcapsules with reticulated HPC walls).

*The comparison of the results obtained with the three lots shows that, unlike what has been observed in the microcapsules of reticulated HPC, the size of the microcapsules does not come much into play (little differences between lots 1 and 3).

*The reticulation time affects the release of the colorant: a clear reduction of the speed of release is observed when going from 3 minutes (lot 3) to 15 minutes (lot 2). Undoubtedly it must be attributed to a reduction of porosity of the membrane associated with the main reticulation.

TABLE I

Release of the patented blue incorporated in the reticulated microcapsules of mixed walls of HPC and casein (concentrations in mg/l)

| Sampling time | Emulsification conditions | | | | | |
|---|---|---|---|---|---|---|
| | LOT 1 | | LOT 2 | | LOT 3 | |
| | speed 1000 rpm | Span 85 ® 2% | speed 1800 rpm | Span 85 ® 5% | speed 1800 rpm | Span 85 ® 5% |
| | Reticulation time | | | | | |
| | 3 minutes | | 15 minutes | | 3 minutes | |
| 30 minutes | 0.55 mg/l | | 0.20 mg/l | | 0.40 mg/l | |
| 1 hour | 0.70 | | 0.20 | | 0.50 | |
| 2 hours | 0.80 | | 0.35 | | 0.70 | |
| 3 hours | 0.90 | | 0.50 | | 0.85 | |
| 4 hours | 1 | | 0.60 | | 0.95 | |
| 5 hours | 1.10 | | 0.65 | | 1 | |
| 6 hours | 1.15 | | 0.70 | | 1.20 | |
| 7 hours | 1.15 | | 0.80 | | 1.25 | |
| 8 hours | 1.20 | | 0.85 | | 1.30 | |
| 24 hours | 1.75 | | 1.50 | | 2.20 | |

EXAMPLE 3

Microcapsules of mixed walls prepared from soluble starch and reticulated casein

Preparation 200 mg alkali-soluble casein are added to 3 ml of a solution of soluble starch at 10 g % in soda 0.5N.

The solution obtained is emulsified in 15 ml of chloroform-cyclohexane mixture (1:4 v/v) to which has been added 0.75 ml of Span 85 ® by stirring for 3 minutes at 1800 rpm.

there are added 20 ml of solution saturated with terephtaloyle chloride in the solvent mixture. After stirring for 10 minutes (1800 rpm), 30 ml solvent mixture are added to the medium.

The microcapsules that have been separated by centrifugation are washed:
1 time with an alcoholic solution of Tween 20 ® at 5% (v/v)
2 times with alcohol
1 time with water

Behavior in the digestive media

Artificial gastric medium
The microcapsules wholly resist at least 8 hours.
Artificial intestinal medium
Lysis starts after about 1 hour and continues progressively (60% lysis after 8 hours).

EXAMPLE 4

Microcapsules of mixed walls prepared from dextrans and reticulated casein

The steps described above are reproduced starting from 3 ml of a solution of dextrans at 5 g % in soda 0.5N to which have been added 20 mg alkali-soluble casein.
Artificial gastric medium
The microcapsules are intact after 8 hours of incubation.
Artificial intestinal medium
Lysis starts after 1 hour and extends for 6 hours (total after 6 hours).

EXAMPLE 5

Microcapsules of mixed walls prepared from gum arabic and reticulated casein

The steps described above are reproduced and applied to 3 ml of a gum arabic solution at 5 g % in soda 0.5N to which have been added 200 mg alkali-soluble casein.
Artificial gastric medium
The microcapsules are intact after 8 hours of incubation.
Artificial intestinal medium
Progressive lysis starts after 1 hour, total in 6 hours.

EXAMPLE 6

Microcapsules of mixed walls prepared from dextrans and reticulated gelatin 150 mg dextrans are dissolved in 3 ml of a gelatin solution at 3 g % in soda 0.5N.
The microcapsules are then prepared following the steps described above.
Artificial gastric medium
No lysis is observed after 8 hours.
Artificial intestinal medium
About 20% of the capsules have undergone lysis after 8 hours.

This invention of course is in no manner limited to the particular modes of operation described above, and it is perfectly possible, without departing from the scope of this invention, to envisage a certain number of variants. It is thus that the relative proportions of the starting polyholoside and casein may vary in large proportions determined in accordance with each particular application. They can, for instance, be determined so as to allow a very quick dissolution in intestinal medium while preserving a perfect gastric resistance. It is in fact the incorporation of the protein in the wall of the microcapsules that is decisive for imparting to the latter the enteric solubility desired.

We claim:
1. A process for preparation of microcapsules having mixed walls containing pharmaceutically active substance, of a water soluble nature comprising:
(i) dissolving a mixture containing at least one water soluble polyhoside or water-soluble derivative of a polyhoside, at least one protein, and the pharmaceutically active substance in an alkaline aqueous solution having a pH preferably above 10, said solution being emulsified by dispersion within an immiscible organic solvent, by addition of an emulsifier of the water in oil type and by stirring;
(ii) adding a reticulation agent dissolved in said immiscible organic solvent to the emulsion thus ob- tained, which is being stirred, continuing said stirring until interfacial reticulation achieved, and (iii) isolating the microcapsules by diluting the reaction mixture by means of a solvent or an adequate mixture of solvents followed by decantation, centrifugation, or a combination thereof, wherein the properties of lysis and gastric resistance are improved relative to microcapsules which are made by the same method and contain only protein or only carbohydrate.

2. A process according to claim 1, wherein the water-soluble polyholoside or water-soluble derivative of polyholoside is selected from the group consisting of water-soluble natural polyholosides, polyholosides made water-soluble by treatment with acid or alkaline solution or by chemical grafting of hydrophilic lateral chains, and mixtures thereof.

3. A process according to claim 2, wherein said water-soluble polyholoside or water-soluble derivative of polyholoside is selected from the group consisting of alkali-cellulose, soluble starch, dextrans of low molecular weight, hydroxypropyl cellulose, gum arabic, gum guar and mixtures thereof.

4. A process according to claim 1, wherein said protein is casein.

5. A process according to claim 1, wherein said protein is gelatin.

6. A process according to claim 1, wherein the organic solvent used during the emulsification stage is a water-immiscible solvent of a density substantially between 0.7 and 1.1, which solvent permits the dissolution of the reticulation agent used during said step (ii).

7. A process according to claim 1, wherein the emulsifier used during the emulsification stages is a surfactant agent, preferably of a non-ionic type, that permits the preparation of an emulsion of a water-in-oil type.

8. A process according to claim 1, wherein said immiscible organic solvent is a binary mixture of a $C_1$-$C_2$ chlorinated hydrocarbon and of a non-chlorinated $C_5$-$C_7$ hydrocarbon.

9. A process according to claim 1, wherein the reticulation agent is an acylating bifunctional reagent selected from the group consisting of carboxylic diacid halides and diisocyanates where the two functional groups are both carried by an aromatic cycle or separated by an aliphatic chain containing from 2 to 10 carbon atoms, or one is carried by an aromatic cycle and the other by a juxtanuclear aliphatic chain.

10. A process according to claim 9, wherein the reticulation agent is selected from the group consisting of succinyl dichloride, sebacoyl dichloride, terephthaloyl dichloride, toluene diisocyanate and hexamethylene diisocyanate.

11. A process according to claim 9, wherein the reticulation agent is added to the reaction mixture dissolved in the same organic solvent used during the first emulsification stage.

12. A process according to claim 1, wherein the concentration of the reticulation agent in said organic solvent changes from saturation to a concentration of about 0.1M.

13. A process according to claim 12, wherein the solution of reticulation agent is added to the emulsion at the rate of a volume substantially equal to the volume of solvent used for the preparation of said emulsion.

14. A process according to claim 1, wherein the microcapsules are recovered in dry state either by evaporation of the washing solvent or solvents or by lyophilization of the suspension of microcapsules in water.

15. A microcapsule prepared according to the process of claim 1.

* * * * *